United States Patent
Fredriksson et al.

(10) Patent No.: US 10,137,314 B2
(45) Date of Patent: Nov. 27, 2018

(54) ROBUST RADIOTHERAPY TREATMENT PLAN GENERATION

(71) Applicant: RaySearch Laboratories AB, Stockholm (SE)

(72) Inventors: Albin Fredriksson, Stockholm (SE); Rasmus Bokrantz, Stockholm (SE)

(73) Assignee: RAYSEARCH LABORATORIES AB, Stockholm (SE)

(*) Notice: Subject to any disclaimer, the term of this patent is extended or adjusted under 35 U.S.C. 154(b) by 18 days.

(21) Appl. No.: 15/524,685

(22) PCT Filed: Nov. 7, 2014

(86) PCT No.: PCT/EP2014/074084
§ 371 (c)(1),
(2) Date: May 5, 2017

(87) PCT Pub. No.: WO2016/070938
PCT Pub. Date: May 12, 2016

(65) Prior Publication Data
US 2018/0117357 A1    May 3, 2018

(51) Int. Cl.
*A61N 5/00* (2006.01)
*A61N 5/10* (2006.01)

(52) U.S. Cl.
CPC .......... *A61N 5/103* (2013.01); *A61N 5/1077* (2013.01)

(58) Field of Classification Search
CPC ..... A61N 5/103; A61N 5/1077; A61N 5/1048
USPC ....................................................... 600/1–8
See application file for complete search history.

(56) References Cited

FOREIGN PATENT DOCUMENTS

| EP | 1 905 482 A1 | 4/2008 |
| WO | WO-2006/130771 A2 | 12/2006 |
| WO | WO-2006/130862 A2 | 12/2006 |

OTHER PUBLICATIONS

Heath, Emily et al., "Incorporating uncertainties in respiratory motion into 4D treatment plan optimization", Medical Physics, AIP, vol. 36, No. 7, Jun. 11, 2009, pp. 3059-3071.
Fredriksson, Albin, "A characterization of robust radiation therapy treatment planning methods—from expected value to worst case optimization", Medical Physics, vol. 39, No. 8, Jul. 31, 2012, pp. 5169-5181.

*Primary Examiner* — John Lacyk
(74) *Attorney, Agent, or Firm* — Drinker Biddle & Reath LLP

(57) ABSTRACT

A method for generating a robust radiotherapy treatment plan, using scenario-based robust optimization, is provided. Weights which are dependent on the overlap of different scenario-specific mappings of a region of interest is used in the optimization.

9 Claims, 5 Drawing Sheets

ROBUST RADIOTHERAPY TREATMENT PLAN GENERATION

This application is the National Stage of International Application No. PCT/EP2014/074084, filed Nov. 7, 2014.

The present invention relates to the field of radiotherapy, and in particular to radiotherapy treatment planning yielding robust treatment plans.

BACKGROUND

In radiotherapy, the goal is typically to deliver a sufficiently high radiation dose to a target (for example a tumor) within the patient, while sparing surrounding normal tissue as far as possible. In particular, it is important to minimize the dose to sensitive organs close to the target. A treatment plan, defining treatment parameters, such as treatment machine settings, to be used in a radiotherapy treatment session, is usually determined with the aid of a computer-based treatment planning system (TPS). In inverse treatment planning, an optimization algorithm is employed for finding a set of treatment parameters that will generate an acceptable dose distribution within the patient, preferably satisfying all the clinical goals defined by the clinician.

Radiotherapy treatment planning is based on medical images, such as three-dimensional CT images. In order to serve as basis for treatment planning, these images must be segmented. Segmentation of an image refers to the process of defining or reconstructing different internal structures or other regions of interest (ROIs) in an image. In the field of radiotherapy, these structures could for example be specific internal organs, or target volumes (such as tumors), which are identifiable in the images.

Preferably, any radiotherapy treatment plan, regardless of the method used to produce the plan, should be robust, meaning that the plan should efficiently take any uncertainties into consideration. Sources of uncertainty include for example uncertainty in the position of the target relative to the beams, uncertainty regarding the location of cancer cells, and uncertainty in the patient density data. Hence, a robust treatment plan must be insensitive to any errors occurring due to such uncertainties.

Traditionally, uncertainties have often been handled by applying margins to ROIs. As a result, treatment planning is based on enlarged volumes, ensuring adequate dose coverage of targets and/or sufficient sparing of risk organs. For example, a margin applied to a Clinical Target Volume (CTV) defines the Planning Target Volume (PTV). In order to limit the dose to healthy tissue as much as possible, the PTV should not be larger than necessary.

Treatment planning using margins is usually considered to be adequate in the field of conventional photon-based radiotherapy within regions of relatively homogeneous density. This is because the "static dose cloud approximation" can be considered to be valid, meaning that a deformation of the patient anatomy has negligible impact on the dose distribution in space. Hence, the patient can be assumed to be moving within a static dose distribution, such that, for example, the effect of a patient setup error corresponds to a rigid translation of the dose distribution. However, the static dose cloud approximation is usually not valid in regions of less homogeneous density, and is usually not suitable for particle radiotherapy, for example using protons or other ions, since the Bragg peak positions (and thus the resulting dose distribution) are highly dependent on the densities of the traversed tissues. The effectiveness of margin-based treatment planning in these situations might therefore be questioned. Nonetheless, the use of margins is still heavily relied upon.

Alternative methods based on a probabilistic approach for achieving robust radiation treatment plans have been proposed, wherein uncertainties are taken into account explicitly in the optimization by considering the (usually unknown) probability distributions of the uncertain parameters when optimizing a treatment plan. In order to yield a computational optimization problem, the possible realizations of the uncertainties are often discretized into a plurality of scenarios, where each scenario corresponds to a specific realization of the uncertainties. As a simple example, different scenarios can be defined by different rigid translations of the patient, corresponding to different possible setup errors. Using an approach based on expected value optimization, the expectation of an objective value over the scenario doses is minimized. Using worst case scenario optimization ("minimax" optimization), the objective function in the worst case scenario (the scenario resulting in the least favorable dose distribution) is minimized. Such, and other, optimization techniques for robust treatment planning are well-known in the art and are discussed for example by A. Fredriksson in "A characterization of robust radiation therapy treatment planning methods—from expected value to worst case optimization" (Med. Phys., 39 (8):5169-5181, 2012). While such methods can produce robust plans also for sites of heterogeneous density, they result in qualitatively different plans than does margin-based planning, even in situations where the static dose cloud approximation holds. For example, using expected value optimization might result in blunt dose fall-offs, i.e. blurred dose distributions, compared to the sharp dose fall-off obtained with margin-based treatment planning. It is generally preferred to have a steep dose fall-off since a blunt fall-off will increase the integral dose to the patient without substantially increasing the probability of tumor control. Using worst case optimization might be too conservative in many situations.

While many methods according to the prior art might result in fairly robust treatment plans in specific cases, there is still much room for improvement, and none of the known methods are, in a satisfying way, universally applicable. For example, methods yielding good results for a "simple" case in a region of relatively homogeneous density might not result in sufficiently robust treatment plans for a complicated case in regions with heterogeneous density (e.g. a lung tumor case). Correspondingly, a method which is suitable for a complicated case might be too conservative for a simpler case, resulting in a suboptimal treatment plan.

An aim of the present invention is to overcome, or at least mitigate, the drawbacks described above, and in particular to provide a treatment planning system that will enable robust treatment plans to be generated for a plurality of different clinical cases and different treatment modalities.

SUMMARY OF THE INVENTION

According to one aspect of the invention, a method for generating a robust radiotherapy treatment plan for a subject at least partly on the basis of a region of interest in the subject is provided. Preferably, the method comprises the steps of:

accessing a set of scenarios comprising at least a first scenario and a second scenario, where each scenario in the set of scenarios represents a specific realization of the uncertainty of one or more parameters relevant for treatment planning;

determining two or more mappings of said region of interest, the two or more mappings comprising at least a first mapping based on said first scenario and a second mapping based on said second scenario;

determining an overlap of said two or more mappings of said region of interest;

calculating at least one weight at least partly on the basis of said overlap;

optimizing an optimization function evaluated over the set of scenarios, wherein the evaluation comprises the use of said at least one weight.

According to another aspect of the invention, a computer program product is provided. Preferably, the computer program product comprises computer-readable instructions which, when executed on a computer, will cause the computer to perform a method for generating a robust radiotherapy treatment plan for a subject at least partly on the basis of a region of interest in said subject, the method comprising the steps of:

accessing a set of scenarios comprising at least a first scenario and a second scenario, where each scenario in the set of scenarios represents a specific realization of the uncertainty of one or more parameters relevant for treatment planning;

determining two or more mappings of said region of interest, the two or more mappings comprising at least a first mapping based on said first scenario and a second mapping based on said second scenario;

determining an overlap of said two or more mappings of said region of interest;

calculating at least one weight at least partly on the basis of said overlap;

optimizing an optimization function evaluated over the set of scenarios, wherein the evaluation comprises the use of said at least one weight.

According to yet another aspect of the invention, a computer system is provided. Preferably, the computer system comprises a processor coupled to a memory having stored thereon computer-readable instructions that, when executed by said processor, cause the processor to perform a method for generating a robust radiotherapy treatment plan for a subject at least partly on the basis of a region of interest in said subject, the method comprising the steps of:

accessing a set of scenarios comprising at least a first scenario and a second scenario, where each scenario in the set of scenarios represents a specific realization of the uncertainty of one or more parameters relevant for treatment planning;

determining two or more mappings of said region of interest, the two or more mappings comprising at least a first mapping based on said first scenario and a second mapping based on said second scenario;

determining an overlap of said two or more mappings of said region of interest;

calculating at least one weight at least partly on the basis of said overlap;

optimizing an optimization function evaluated over the set of scenarios, wherein the evaluation comprises the use of said at least one weight.

An advantage of using weights based on an overlap of scenario-specific mappings of the ROI when optimizing a treatment plan in accordance with the present invention is that robust treatment plans of high quality can be achieved for a large number of different clinical cases.

According to some embodiments, the first and second mappings are determined as functions of dose distributions and/or density distributions corresponding to said first and second scenarios, respectively. Thereby, weights would be determined on the basis of the actual dose- or density distributions corresponding to the different scenarios. In photon treatment cases in regions of relatively uniform density, such as prostate cancer cases, the method would result in a treatment plan closely corresponding to a plan determined using conventional margin-based treatment planning, where the union of all mapped versions of the region of interest (e.g. the CTV) would essentially correspond to a region expanded by an appropriately selected margin (e.g. the PTV). On the other hand, in a more complicated case in a region of heterogeneous density where the static dose cloud approximation would not be valid, the method would automatically result in a robust treatment plan based on the actual dose- or density distributions according to the different scenarios.

According to some embodiments, the step of determining the overlap of the mappings of the region of interest comprises identifying the number of scenarios under which a sub-region in a scenario is located within a corresponding mapping of said region of interest. Such analysis is preferably conducted for a plurality of sub-regions. Thereby, a computationally efficient quantification of the overlap is obtained, which is readily applicable for specifying the weights used in the optimization. Using weights based on the reciprocal of the number of scenarios thus identified would ensure that sub-regions at the border of a CTV in extreme scenarios would be given an increased weight, thereby favoring plans which have a steep dose falloff at the border of the treated target region.

According to some embodiments, a calculated weight is specific for a particular beam, or sub-beam, of radiation. Thereby, beams (or sub-beams) are considered independently, and errors which affect different beam doses differently are taken into account in an appropriate way.

Further aspects of the invention will become apparent by consideration of the detailed description and accompanying drawings. These are only for purposes of illustrating preferred embodiments and are not to be construed as limiting the invention.

DETAILED DESCRIPTION

For illustrative purposes, the FIGS. 2, 3, 4a-c, 5a-d and 6a-c show two-dimensional cross sections of an internal image of a subject (such as a human patient), e.g. representations of single slices of a CT scan. This is merely for facilitating understanding of the invention and it is emphasized that an image used for treatment planning usually comprises many slices defining a three-dimensional representation of the subject.

Figure 1:
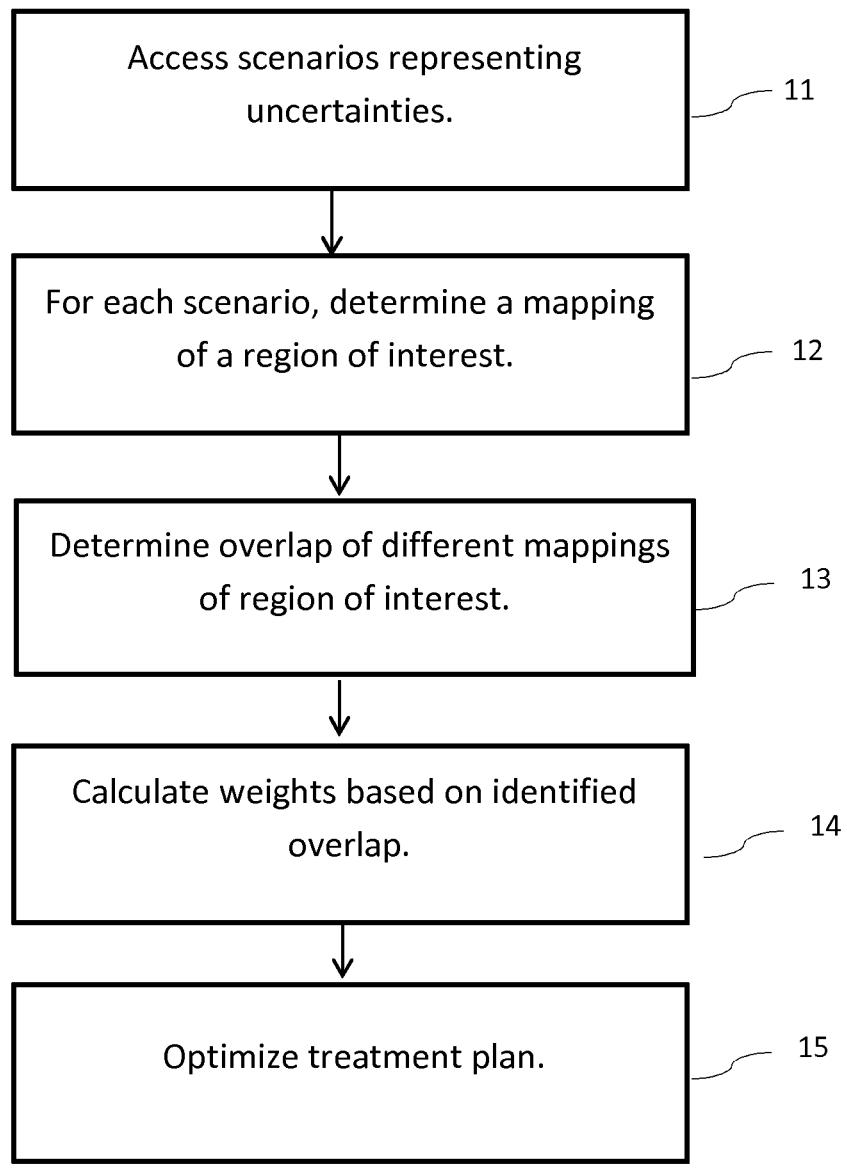
FIG. 1 is a flowchart of a method according to an embodiment of the invention.
Figure 2:
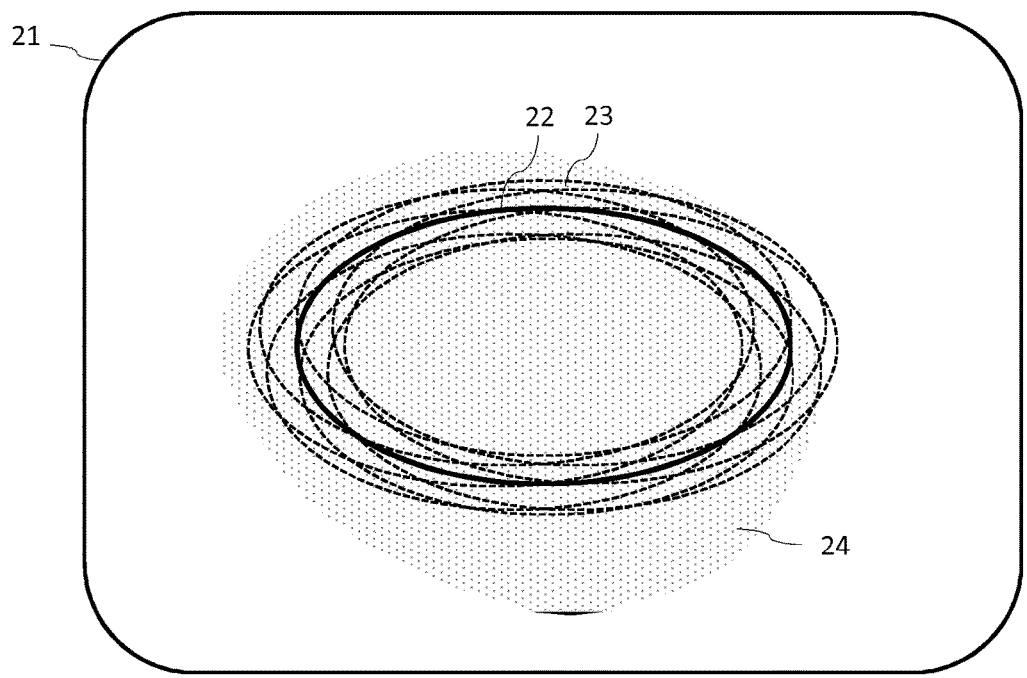
FIG. 2 illustrates an example of different scenarios, representing geometrical uncertainties, and mappings of a region of interest in accordance with (i.e. as a function of) these scenarios.
Figure 3:
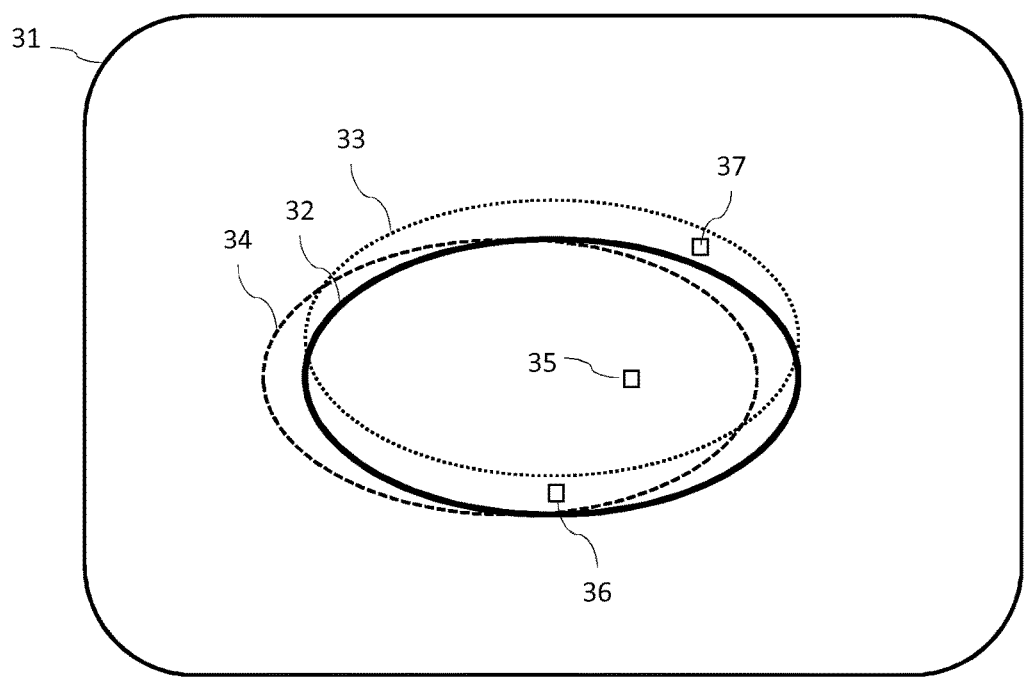
FIG. 3 illustrates sub-regions being located within one or more of mapped regions of interest, and how weights for sub-regions and scenarios can be based thereupon.

A method according to an example embodiment of the invention will now be described with reference to FIG. 1, being a flow-chart indicating the steps of a method according to the invention, and FIGS. 2 and 3, schematically illustrating the application of the method in an example of a simplified case for which the static dose cloud approximation is considered to be valid.

In step 11 shown in FIG. 1, scenarios representing uncertainties, typically in relation to the internal geometry of a patient as recognized in an image used for treatment planning, such as a computed tomography (CT) image of the patient, are accessed, e.g., from a memory of a computer. Scenarios could be defined manually by a user, or automatically on the basis of some input regarding estimated uncertainties. Alternatively, scenarios could be defined automatically without the need of any user interaction, for example by comparing patient or image specific data with reference cases comprising pre-defined scenarios indicating best practice for different situations. The present disclosure is not limited to any specific mechanisms for defining the scenarios or for estimating uncertainties. Nor is the disclosure limited to some specific kind of uncertainty, but is readily applicable in relation to any kind of uncertainty relevant for treatment planning, including range uncertainties, patient setup uncertainties and organ motion and deformation.

In step 12, a mapping of a region of interest is determined, for each scenario, as a function of the scenario.

FIG. 2 illustrates a patient image 21 with a clinical target volume (CTV) 22 defined therein indicated by a solid ellipse, and a set of eight additional scenarios 23 that represent movement of the CTV indicated by dashed ellipses. According to this example, patient setup uncertainties are taken into account. A dose distribution 24 planned for the nominal scenario (i.e. corresponding to the non-shifted CTV 22) is schematically illustrated with dots. As long as the static dose cloud approximation is considered to be valid, the effect of the patient shifts would correspond to rigidly moving the CTV within the dose distribution 24 as shown in the figure. Hence, the set of additional scenarios 23 corresponds to rigid patient shifts in different directions and represents a patient setup uncertainty at the time of treatment. Accordingly, each of the ellipses 23 represents a mapping of the CTV as a function of the corresponding scenario.

Referring again to FIG. 1, in step 13, an overlap of different scenario-dependent mappings of the region of interest is identified. "Overlap" as used herein relates to the extent or degree of, or the non-existence of, a geometrical intersection between different regions. One exemplary way to quantify such overlap could be to identify the number of scenarios under which a specific sub-region is located within a corresponding mapping of the region of interest. Advantageously, such analysis is made for a plurality of sub-regions of the image. Another exemplary way to quantify such overlap is to quantify the intensities of the different regions that are intersected. A medical image used for treatment planning is usually discretized into a number of volume elements, or "voxels". Hence, sub-regions could for example correspond to voxels in the image. The step 13 is further illustrated with reference to FIG. 3.

FIG. 3 shows a situation where the conditions are similar to those described previously with reference to FIG. 2, i.e. wherein a static dose cloud approximation is valid and where mappings of a CTV 32 as a function of the scenarios simply correspond to rigid translations (i.e. shifts) of the CTV within the patient image 31. In FIG. 3, only two shift scenarios (in addition to the nominal scenario represented by the non-shifted CTV 32 indicated by a solid ellipse) are shown. The first shift scenario is defined by a shift in a first direction and is represented by a dotted ellipse 33. The second shift scenario is defined by a shift in a direction perpendicular to the first direction, and is represented by a dashed ellipse 34. For each voxel in the image, the number of scenarios in which the voxel is located within the correspondingly mapped CTV is ascertained. For example, the voxel 35 is located within the CTV of the nominal scenario and in the mapped CTVs of both the additional shift scenarios. The voxel 36 is located within the CTV of the nominal scenario and in the mapped CTV of the second shift scenario represented by the ellipse 34. The voxel 37 is only located within the mapped CTV according to the first shift scenario represented by the ellipse 33.

With continued reference to FIG. 1, in step 14, weights are determined on the basis of identified overlaps. In view of the exemplary embodiment described with reference to FIG. 3, the weight for each sub-region in a scenario is determined on the basis of the number of identified scenarios under which a specific sub-region is located within a correspondingly mapped region of interest.

The rationale for selecting weights in accordance with these teachings, will be clarified in the following example, wherein an arbitrary voxel-separable dose-based penalty function $\phi$ is considered. Such a function, when applied to a planning target volume (PTV), induces the penalty $$\sum_{i \in P} \phi(d_i), \qquad (1)$$

where $d_i$ is the dose to voxel i and the set P enumerates the PTV voxels. Some commonly used voxel-separable functions include minimum, maximum, and uniform dose penalties. As a simple example, if using an optimization function involving uniform dose penalty, $\phi(d_i)$ could be defined as $$\phi(d_i) = \left(\frac{d_i - d^{ref}}{d^{ref}}\right)^2$$

where $d_i$ is the dose in voxel i and $d^{ref}$ is the reference dose. The dose $d_i$ is a function of the treatment parameters which are to be determined by the optimization, and the reference dose $d^{ref}$ is the dose objective relating to a desired dose in the ROI. Using an optimization function involving such a penalty, both under- and overdosage with respect to the reference dose level are equally penalized. This is only one example, and, as would be apparent to a person skilled in the art, many alternative optimization functions involving various kinds of dose penalties may be employed. The use of optimization functions involving dose-based penalties is well-known in the art of radiotherapy treatment planning and will therefore not be further described herein.

According to the static dose cloud approximation, the effect of a setup error is that the patient is shifted rigidly inside a static dose distribution. A rigid shift of the patient corresponds to the voxel indices being shifted by a fixed offset (assuming that the shift lines up with the dose grid). Let S be the set of scenarios and let the offset corresponding to the shift of scenario s in S be denoted by j(s). The CTV voxels under scenario s are then given by the scenario-dependent set C(s):={i+j(s):i∈C}, where C enumerates the CTV voxels in the nominal scenario (corresponding to no error). Because the PTV is an expansion of the CTV it then holds that P=∪$_{s∈S}$C(s) if S is appropriately defined. Note that this equivalency is assumed merely for the purpose of showing that scenario-based optimization according to the invention is essentially equivalent to margin-based treatment planning for the specific situation where a static dose cloud approximation holds, and it does not imply any actual requirements on the scenario selection. Any set of scenarios which is considered to be an appropriate representation of the uncertainty can be used in the context of the present invention. In any case, using this assumption, the penalty (1) can be equivalently stated as $$\sum_{i\in \cup_{s\in S} C(s)} \phi(d_i).$$

This, in turn, is equivalent to $$\sum_{s\in S}\sum_{i\in C(s)} p_i \phi(d_i),$$

where $p_i$ is the reciprocal of the number of scenarios s under which voxel i is in C(s), i.e., $$p_i = \frac{1}{|\{s\in S: i\in C(s)\}|},$$

where |•| denotes the number of elements in the set. Offsetting the voxel indices within a fixed dose distribution is equivalent to keeping the voxel indices fixed but shifting the dose rigidly; this penalty can also be formulated as $$\sum_{s\in S}\sum_{i\in C} p_{i+j(s)} \phi(d_{i+j(s)}).$$

If we denote the dose to voxel i under scenario s by $\tilde{d}_i(s):=d_{i+j(s)}$, and the corresponding weight by $p_{i,s}:=p_{i+j(s)}$, then the penalty can be written $$\sum_{s\in S}\sum_{i\in C} p_{i,s} \phi(\tilde{d}_i(s)), \quad (2)$$

which is our scenario-based reformulation of the PTV penalty. To summarize, we derived the following equivalence:

$$\sum_{i\in P} \phi(d_i) = \sum_{s\in S}\sum_{i\in C} p_{i,s} \phi(\tilde{d}_i(s)),$$

where $\tilde{d}_i(s)=d_{i+j(s)}$ and $$p_{i,s} = \frac{1}{|\{s'\in S: i+j(s)-j(s')\in C\}|}. \quad (3)$$

Note that by applying a function ψ to both sides of the derived equivalence, functions of voxel-separable functions (such as equivalent uniform dose functions) can be handled with the exact same framework as described above. Furthermore, a similar approach is applicable also if using voxel-specific penalty functions $\phi_i(d_i)$, i.e. where the reference dose level is specific, and possibly different, for each voxel in the ROI.

According to the exemplary embodiment of the invention as described above, a voxel- and scenario-specific weight (3) is proportional to the reciprocal of the number of scenarios under which the voxel is located within the corresponding rigidly shifted CTV. This identified number of scenarios for the different voxels in different scenarios represents the overlap of the plurality of mappings of the region of interest (i.e. the plurality of rigid shifts of the CTV according to this example). Accordingly, as a simple example with reference to FIG. 3, the weight $p_{i,s}$ used for voxel 36 in the second scenario would be calculated as 1/(number of identified scenarios)=½.

In the previously described examples, the penalty (2) is derived under the assumption that a static dose cloud approximation is valid. However, by using the penalty (2) together with the real dose distribution of scenario s, denoted by d(s), in place of the dose distribution d̃(s) of the static dose cloud approximation, a more universally applicable penalty function would be obtained:

$$\sum_{s\in S}\sum_{i\in C} p_{i,s} \phi(d_i(s)), \quad (4)$$

In cases where the static dose cloud approximation holds, this means that the penalty will be essentially equivalent to using a PTV; but in cases where the static dose cloud approximation does not hold, the penalty will be defined on the basis of the true dose distribution. Hence, using the penalty (4), the method would be applicable for any kind of case and any kind of uncertainty.

Again referring to FIG. 1, in step 15, a treatment plan is generated. This step comprises optimization of an optimization function (e.g. the sum of φ over the voxels) evaluated over the set of defined scenarios, wherein the evaluation comprises the use of weights as calculated in accordance with the above. For example, an objective function (usually a sum of different optimization functions regarding various treatment objectives relating to different regions of interest) comprising an optimization function based on the penalty (4), can be optimized. For the optimization, various different techniques may be employed. For example, gradient-based methods, such as methods based on sequential quadratic programming algorithms, or heuristic methods, such as simulated annealing, can be used. For photon-mediated treatments, the optimization might be fluence-based, which requires subsequent conversion to machine parameters, or based on Direct Machine Parameter Optimization (DMPO) where machine parameters are directly optimized, or a combination of both. Using protons or other ions as the treatment modality, the optimization might comprise optimizing spot weights. Optimization of an objective function is well-known in the art of radiotherapy treatment planning and will therefore not be described in further detail herein. The present disclosure is not limited to any specific technique for optimization.

Figure 4A:
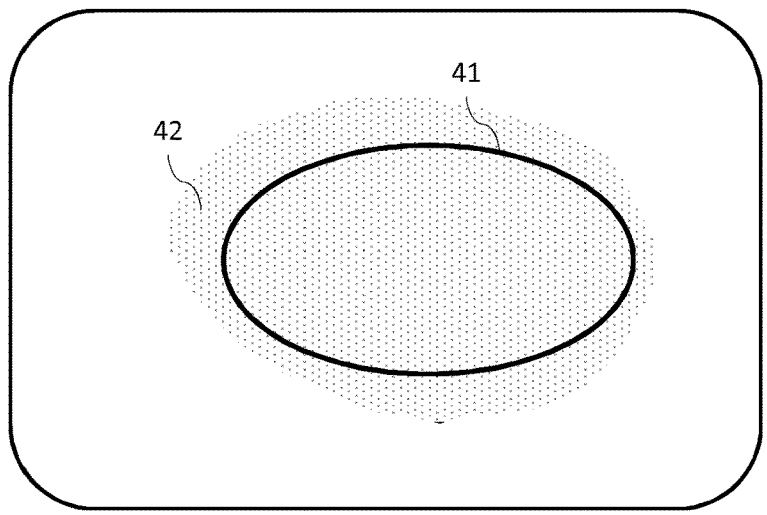
FIGS. 4a-c illustrates an example of a mapping of a region of interest as a function of a scenario.
Figure 4B:
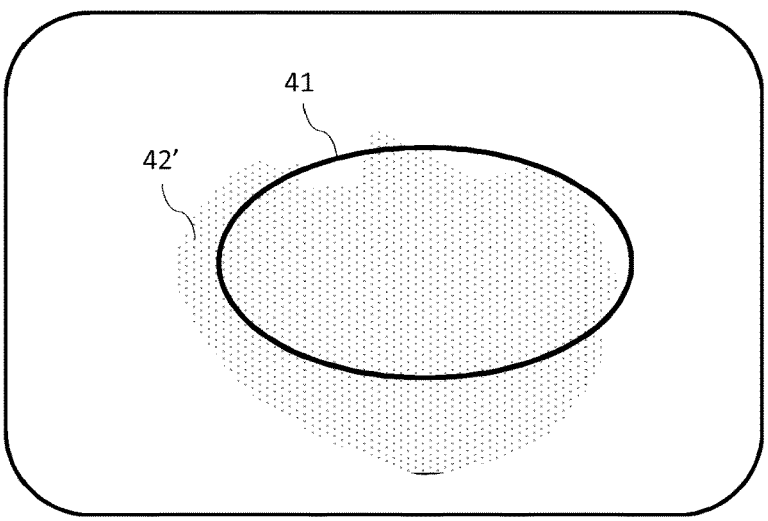
Figure 4C:
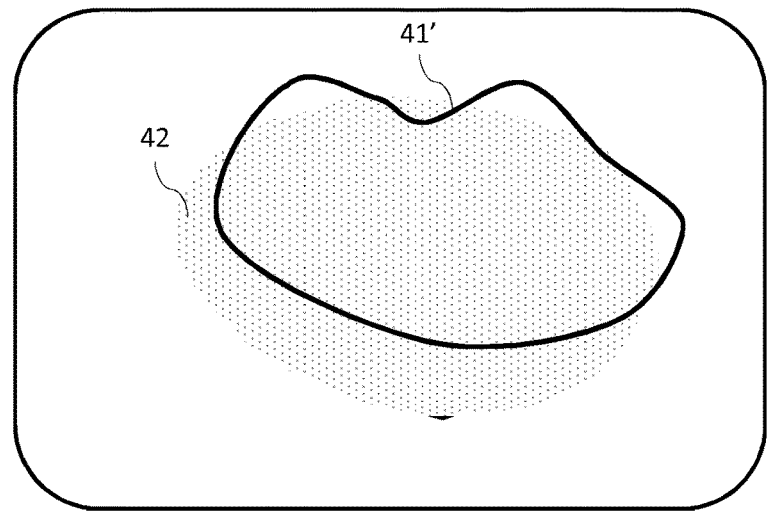

Reference is now made to FIG. 4a-c further illustrating the effect of using an optimization function based on the penalty (4) when planning treatments for regions of heterogeneous density, or in other situations where the dose distribution will change substantially due to uncertainties. In such situations, a dose distribution of a scenario might be deformed as a result of patient setup errors, range errors (e.g. due to errors in the image CT-to-density conversion), deformations of internal organs, etc. FIG. 4a illustrates a CTV 41 and a dose distribution 42 determined on the basis of the nominal scenario, i.e. without any errors. FIG. 4b illustrates the resulting dose distribution 42' as it would appear in a different scenario, for example defined by some specified deformation or motion of organs in the vicinity of the CTV. As seen in the figure, the dose distribution 42' has been significantly deformed, and a rigid shift of the CTV 41 within the dose distribution would not be an appropriate representation of the scenario. However, such deformed dose distribution could instead be interpreted as a deformed CTV 41' in the dose distribution 42 of the nominal scenario, as would be apparent to a person skilled in the art. In FIG. 4c, a deformed CTV 41', transformed in accordance with the scenario dose distribution 42', is illustrated in relation to the nominal dose distribution 42. Note that this drawing is merely for illustrative purposes and is not necessarily a realistic representation of a CTV deformed in accordance with the deformed dose distribution 42'. By using this method for deforming the region of interest, and thereby obtain, in relation to the nominal dose distribution, a mapping of the region as a function of the scenario, an analysis regarding the overlap of different mappings of the CTV can be made in a corresponding way as described previously with reference to FIG. 3.

In some embodiments, where scenarios are defined on the basis of different density distributions (i.e. where errors in the density distribution, for example due to errors in the CT-to-density conversion, are considered in different scenarios), a mapping of the region of interest can be defined directly as a function of a density distribution. Hence, as an example with reference to FIGS. 4b and 4c, if assuming that the deformed dose distribution 42' is an effect of a modified density distribution, a deformed CTV 41' could be determined directly as a function of the modified density distribution instead of as a function of a dose distribution.

According to some embodiments of the invention, weights are not only dependent on the overlap of scenario-specific mappings of a ROI, but are also beam dependent. The rationale for this is that errors might affect different beam doses differently. If, e.g., a setup shift occurs that is parallel to the incidence direction of a given beam, this will only affect the dose distribution marginally (by scaling according to the inverse square law). On the other hand, if the shift is perpendicular to the beam direction, the effect is often large. To take this into account, the beams could be considered independently. Hence, as an example, beam-specific weights $p_{i,s}^b$ for the beams b in the set B of all beams, could be defined. The definition of the weights $p_{i,s}^{(b)}$ can be stated as (3), but with $j^{(b)}$ substituted for j. Here, $j^{(b)}(s)$ is the offset in the dose grid corresponding to the shift of scenario s projected onto the beam plane (recall that j(s) was defined in the same way but without the projection onto the beam plane). Thus $j^{(b)}(s)$ neglects setup errors parallel to the direction of the beam. The voxel weights of different beams can be combined into a single weight, e.g., by interpolation.

If the dose of beam b delivered to voxel i under scenario s is denoted by $d_i^{(b)}(s)$, the penalty to voxel i under scenario s can be defined as $$\sum_{b \in B} \frac{d_i^{(b)}(s)}{d_i(s)} p_{i,s}^{(b)} \phi(d_i(s)), \qquad (5)$$

where $$\frac{d_i^{(b)}(s)}{d_i(s)}$$

is taken as $$\frac{1}{|B|}$$

whenever $d_i(s)=0$.

Figure 5A:
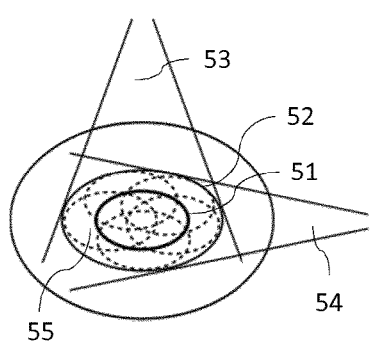
FIG. 5a-c illustrates an example of how beam-specific mappings and weights can be determined.
Figure 5B:
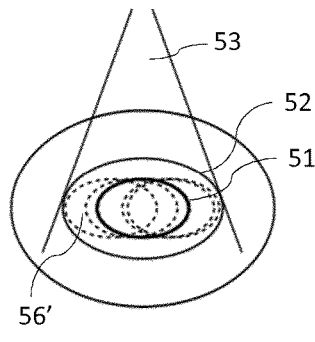
Figure 5C:
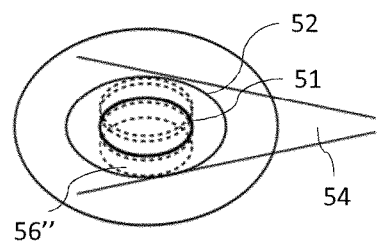

FIG. 5a-c illustrates how beam-specific weights can be determined in accordance with the above. FIG. 5a shows a CTV 51 and a first beam 53 and a second beam 54 for treating the CTV 51. A margin 52 indicates the PTV which would have been used for conventional margin-based planning. A set of five scenarios 55, for example corresponding to possible setup errors, is shown with dashed lines. FIG. 5b shows the scenario mappings (i.e. shifts) of the CTV 51 projected onto the beam plane for the first beam 53, resulting in a set of mappings 56' of the CTV which are specific for the first beam 53. Correspondingly, FIG. 5c shows the scenario mappings of the CTV 51 projected onto the beam plane for the second beam 54, resulting in a set of mappings 56" of the CTV which are specific for the second beam 54. Hence, when using beam-specific weights, multiple CTV mappings (one for each beam) for each scenario will be determined. Thereafter, for each voxel, scenario and beam, the number of scenarios under which the voxel is located within a correspondingly mapped and projected CTV is determined and used as basis for calculating the voxel-, scenario- and beam-specific weight (e.g. as the reciprocal of the number of identified scenarios).

Because ion range errors affect the beams differently, some means of beam-specificity is advantageous to use in order to take such errors into account in the definition of voxel- and scenario-specific weights. For a scenario s constituted by a setup and a range error, the offset $j^{(b)}(s)$ could be separated into a lateral part and a longitudinal part (in the beam plane). The lateral part would be defined by the setup error projected onto the beam plane, and the longitudinal part would be defined by the range error. Moreover, the offset for voxel i could be defined as $j_i^{(b)}(s)$, i.e., not only dependent on the beam and scenario, but also on the voxel index. This permits taking into account the effect that voxels located distally from the beam source are more highly affected by range uncertainty than proximally located voxels. Clearly, such voxel-specific offsets could also be used to define elaborate mappings for other types of errors than range errors.

According to some embodiments of the invention, each constituent, or "sub-beam", of the beam dose distribution can be considered as an independent beam. For example, a sub-beam can refer to a beamlet dose distribution for photon-based treatment, and to a spot dose distribution for scanned ion therapy. Hence, this yields an expression for the penalty to voxel i that is on the form of the penalty (5), but with B representing the set of all sub-beams and $d_i^{(b)}(s)$ being the dose to voxel i from sub-beam b in scenario s. The sub-beam specific approach can be advantageous if there are large differences regarding how the different sub-beam dose distributions become deformed under different realizations of uncertainty.

If the scenarios are not only rigid setup errors or uniform range errors, e.g. if a scenario is based on non-uniform range errors or organ motion, a more general approach could be taken when considering beam-specific weights. A generalization of the beam-specific weights defined above is achieved when each scenario is considered to be an independent image of the patient. The patient geometry can thus deform without restriction between scenarios. To calculate whether the CTV overlaps between scenarios in the view of a given beam, the position of the CTV projected onto the beam plane is combined with the radiological depth of each voxel within the CTV from the direction of the considered beam.

Figure 6A:
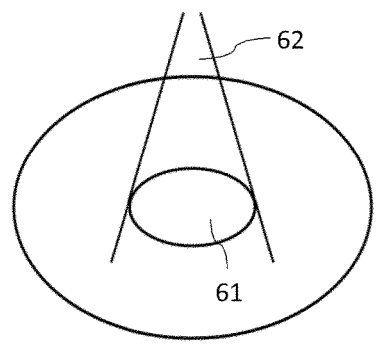
FIG. 6a-d illustrates an example of how an overlap can be determined in a situation where scenarios are considered as independent images of the subject.
Figure 6B:
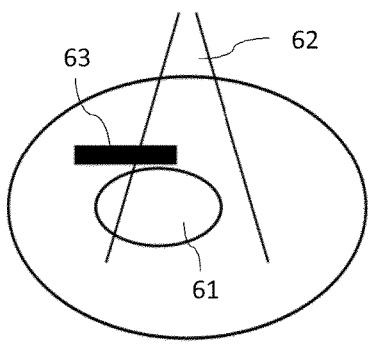
Figure 6C:
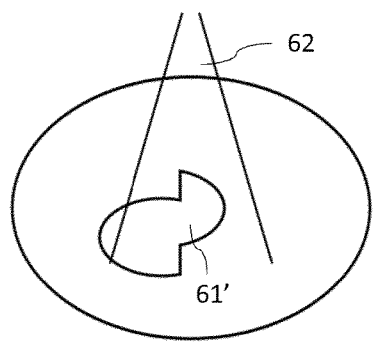
Figure 6D:
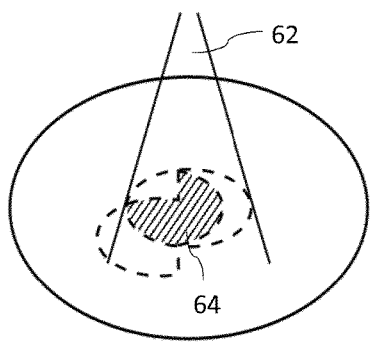

This is illustrated in FIGS. 6a-d, showing how an overlap of two scenario-specific mappings of a CTV is established when considering the scenarios as independent images of the patient. FIG. 6a shows a first scenario wherein treatment of a CTV 61 in a first position is planned using radiation beam 62. In the second scenario shown in FIG. 6b, the CTV 61 has moved laterally to a second position, and a high-density region 63 has partly moved into the radiation beam path, affecting the radiological depth of a part of the CTV. A mapping 61' of the ROI, determined as a function of the second scenario, is shown in FIG. 6c. In relation to the ROI 61 according to the first scenario, the resulting mapped ROI 61' is not only shifted, but also partly deformed due to the altered radiological depth caused by the high-density region 63. FIG. 6d illustrates the overlap 64 of the ROI 61 in the first scenario and the ROI 61' mapped from the second scenario. Based on the overlap 64, the weights employed in the treatment plan optimization can be calculated as described elsewhere herein. The sub-beam specific representation discussed above is directly compatible with a deformation that incorporates radiological depths.

Further more elaborate embodiments of the invention take into account how the dose contribution to each voxel from a sub-beam becomes deformed in the different scenarios. Denote by D(s) the dose-influence matrix for scenario s such that the element $D_{ib}(s)$ at row i and column b is the dose to voxel i in scenario s from sub-beam b at unit weight. Moreover, denote by $A^{(b)}(s, t)$ a deformation matrix for sub-beam b and the pair of scenarios (s, t) from S such that the element $A_{ij}^{(b)}(s, t)$ is the fraction of the dose contribution to voxel i in scenario s from unit irradiation with sub-beam b that becomes displaced to voxel j in scenario t. Then, a penalty that takes into account how the individual voxel dose contributions become deformed can be defined by penalty (5) above, with $p_{i,s}^{(b)}$ defined as the ratio between the dose contribution to voxel i from sub-beam b in scenario s at unit weight and the fraction of this dose contribution that is displaced to voxel j in scenario t, integrated over all scenarios t in S and voxels j in the CTV, i.e., $$p_{i,s}^{(b)} = D_{ib}(s) \bigg/ \sum_{t \in S} \sum_{j \in C} A_{ij}^{(b)}(s, t) D_{jb}(t).$$

The weight $p_{i,s}^{(b)}$ is thus defined on the basis of the overlap between the CTV and the voxel dose contributions of sub-beam b that correspond to each other over the scenarios. Here, the dose contribution i of beam b is taken as the region of interest and $A^{(b)}(s, t)$ defines the mapping of the region of interest between scenarios s and t.

According to all of the example embodiments discussed above, a discrete set of scenarios has been considered. However, in other embodiments, an infinite set of scenarios (e.g. a continuous set of scenarios) is used instead. As would be apparent to the person skilled in the art, in such an approach the overlap of scenario-specific mappings would not correspond to a number of scenarios under which a voxel is located within corresponding mappings of the ROI, but rather to a probability that a voxel (or any other spatial sub-region considered) is within the ROI.

Figure 7:
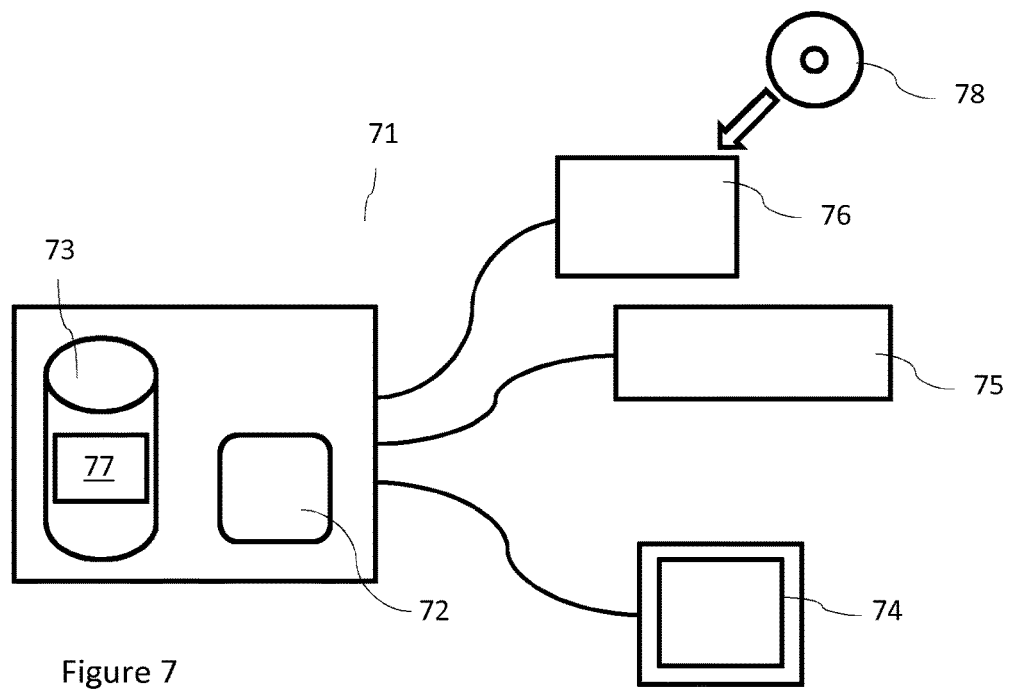
FIG. 7 is a schematic illustration of a computer system according to an example embodiment of the invention.

FIG. 7 schematically illustrates an example of a computer system 71 according to the invention. The system comprises a processor 72, coupled to a memory 73. Furthermore, the system can include a display device 74 (e.g. for displaying patient images and dose distributions, a graphical user interface, and any other information related to treatment planning), a data input device 75 (e.g. a keyboard, a mouse or any other suitable device for data input) and a data reading/writing device 76 (e.g. an optical drive, USB interface, or any other suitable device for reading/writing data). The processor 72 can be of any kind, such as one or more central processing units (CPU) or any kind of parallel processor system, e.g. based on one or more graphics processing units (GPU). The memory 73 can be any kind of volatile or non-volatile memory suitable for storing and retrieving information, such as, for example, any kind of random access memory (RAM) or hard disk drive. The memory 73 has a computer program 77 stored thereon. The memory 73 can also have additional data stored thereon, such as, for example, information regarding various scenarios used for treatment planning, defined on the basis of an uncertainty of one or more parameters. The computer program 77 comprises computer-readable instructions for generating the robust radiotherapy treatment plan, where the computer-readable instructions can be transferred to, and executed by, the processor 72. When executed by the processor 72, the computer-readable instructions will cause the method for generating a robust treatment plan to be performed, the method comprising optimization of a function evaluated over a set of scenarios employing weights determined on the basis of identified overlap of different scenario-specific mappings of a ROI. A thereby generated treatment plan can be stored on the memory 73. The computer program 77 can also be stored on a non-transitory computer readable medium 78, e.g. a USB drive, an optical data carrier such as a CD-ROM, or any other suitable portable information storage device, so that the computer program 77 can be loaded to the memory 73 and/or transferred to different computing systems. The system described with reference to FIG. 7 is merely an example, and a computer system according to the invention does not necessarily comprise all the illustrated components, and/or might comprise other components not illustrated.

The invention has been described with reference to a number of example embodiments. It is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

For example, the method can be applied in view of any type of errors, such as organ motion or deformation or ion range errors. Furthermore, even though a single target has been considered in the example embodiments, the method can be readily applied to multiple organs, including organs at risk (OARs).

Moreover, in the example embodiments it has been assumed that all setup error scenarios correspond to geometrical shifts that can be represented by vectors with all components being multiples of the voxel dimensions. This assumption simplifies the presentation, but can be alleviated by the use of interpolation.

Furthermore, while the example embodiments refer to using optimization functions involving voxel-separable dose penalties, the use of other kinds of penalty functions are envisaged, such as dose volume histogram (DVH) based functions. Such functions could be readily incorporated in a robust optimization method according to the present invention using similar approaches as those discussed above.

The invention claimed is:

1. A method for generating a robust radiotherapy treatment plan for a subject at least partly on the basis of a region of interest in said subject, the method comprising the steps of:
   accessing a set of scenarios comprising at least a first scenario and a second scenario, where each scenario in the set of scenarios represents a specific realization of the uncertainty of one or more parameters relevant for treatment planning;
   determining two or more mappings of said region of interest, the two or more mappings comprising at least a first mapping based on said first scenario and a second mapping based on said second scenario;
   identifying a number of scenarios of said set of scenarios under which a specific sub-region is located within a corresponding mapping of said region of interest;
   calculating a weight for the specific sub-region, at least partly on the basis of the number of scenarios identified; and
   optimizing the treatment plan by optimizing an optimization function evaluated over the set of scenarios, wherein the evaluation comprises the use of said weight.

2. The method according to claim 1, wherein said first and second mappings are determined as functions of dose distributions and/or density distributions corresponding to said first and second scenarios, respectively.

3. The method according to claim 1, wherein said weight is specific for a particular radiation beam.

4. A computer program product comprising computer-readable instructions which, when executed on a computer, causes the computer to perform a method for generating a robust radiotherapy treatment plan for a subject at least partly on the basis of a region of interest in said subject, the method comprising the steps of:
   accessing a set of scenarios comprising at least a first scenario and a second scenario, where each scenario in the set of scenarios represents a specific realization of the uncertainty of one or more parameters relevant for treatment planning;
   determining two or more mappings of said region of interest, the two or more mappings comprising at least a first mapping based on said first scenario and a second mapping based on said second scenario;
   identifying a number of scenarios of said set of scenarios under which a specific sub-region is located within a corresponding mapping of said region of interest;
   calculating a weight for the specific sub-region at least partly on the basis of the number of scenarios identified; and
   optimizing the treatment plan by optimizing an optimization function evaluated over the set of scenarios, wherein the evaluation comprises the use of said weight.

5. The computer program product according to claim 4, wherein said first and second mappings are determined as functions of dose distributions and/or density distributions corresponding to said first and second scenarios, respectively.

6. The computer program product according to claim 4, wherein said weight is specific for a particular radiation beam.

7. A computer system comprising a processor coupled to a memory having stored thereon computer-readable instructions that, when executed by said processor, cause the processor to perform a method for generating a robust radiotherapy treatment plan for a subject at least partly on the basis of a region of interest in said subject, the method comprising the steps of:
   accessing a set of scenarios comprising at least a first scenario and a second scenario, where each scenario in the set of scenarios represents a specific realization of the uncertainty of one or more parameters relevant for treatment planning;
   determining two or more mappings of said region of interest, the two or more mappings comprising at least a first mapping based on said first scenario and a second mapping based on said second scenario;
   identifying a number of scenarios of said set of scenarios under which a specific sub-region is located within a corresponding mapping of said region of interest;
   calculating a weight for the specific sub-region, at least partly on the basis of the number of scenarios identified; and
   optimizing the treatment plan by optimizing an optimization function evaluated over the set of scenarios, wherein the evaluation comprises the use of said weight.

8. The computer system according to claim 7, wherein said first and second mappings are determined as functions of dose distributions and/or density distributions corresponding to said first and second scenarios, respectively.

9. The computer system according to claim 7, wherein said weight is specific for a particular radiation beam.

* * * * *